United States Patent [19]
Goldstein et al.

[11] Patent Number: 6,150,358
[45] Date of Patent: Nov. 21, 2000

[54] 1,2-DITHIOLANE COMPOUNDS

[75] Inventors: Solo Goldstein, Suresnes; Claude Guillonneau, Clamart; Yves Charton, Sceaux; Pierre Lestage, La Celle Saint Cloud; Brian Lockhart, Croissy sur Seine, all of France

[73] Assignee: Adir et Compagnie, Courbevoie, France

[21] Appl. No.: 09/460,596

[22] Filed: Dec. 14, 1999

[30] Foreign Application Priority Data

Dec. 15, 1998 [FR] France .................................. 98 15821

[51] Int. Cl.⁷ ....................... A61K 31/5377; A61P 25/28; C07D 413/12
[52] U.S. Cl. ........................................ 514/231.5; 544/145
[58] Field of Search .......................... 544/145; 514/231.5

[56] References Cited

U.S. PATENT DOCUMENTS 6,013,663  1/2000  Fujita et al. ............................ 514/445

*Primary Examiner*—Robert W. Ramsuer
*Attorney, Agent, or Firm*—The Firm of Hueschen and Sage

[57] ABSTRACT

A compound of formula (I):

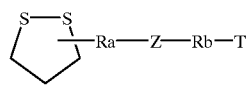

(I)

wherein
   Ra represents linear or branched $(C_1-C_8)$alkylene,
   Rb represents single bond, or linear or branched $(C_1-C_6)$ alkylene,
   Z represents thiocarbamate, or thioamide, each being optionally substituted,
   T represents optionally substituted morpholino,
its isomers, and pharmaceutically-acceptable acid or base addition salts thereof, and medicinal products containing the same which are useful in the treatment of disease for which the use of anti-oxidation agent is required.

14 Claims, No Drawings

1,2-DITHIOLANE COMPOUNDS

FIELD OF THE INVENTION

The present invention relates to new 1,2-dithiolane compounds.

These new compounds are antioxidants, traps for reactive oxygenated species, which are capable of combating "oxidation stress" in the cerebral region.

According to Hartman's free-radical theory of ageing, successive oxidation attacks create "oxidation stress" conditions, that is to say create an imbalance between the protective systems in favour of the pro-oxidants.

Such attacks result in numerous molecular modifications, especially of polyunsaturated membrane lipids, proteins and nucleic acids. Human and animal organisms possess various defence mechanisms that act in synergy. Those mechanisms are of an enzymatic nature (superoxide dismutase, catalase, glutathione peroxidase) or of a non-enzymatic nature (such as vitamins E and C, which enable physiological control of free-radical activity). With age, however, that protection becomes less efficient, not to say inefficient, especially as a result of the oxidative inactivity of a large number of enzymes including those involved in such defence mechanisms. Consequently, for some disorders associated with ageing, such as atherosclerosis, cataract, non-insulin-dependent diabetes, cancer or chronic neurodegenerative disorders, numerous studies have been able to demonstrate that such disorders are associated with those "oxidation stress" conditions.

The central nervous system is especially sensitive to "oxidation stress" because of its high oxygen consumption, the relatively low levels of its anti-oxidation defences and the high iron content of some cerebral regions. This explains why "oxidation stress" might be one of the main etiological factors of cerebral ageing, as well as of chronic neurodegenerative disorders, especially Alzheimer's disease and neurodegeneracies of the basal ganglia.

In addition to the fact that the compounds of the present invention are new, they have proved to be more powerful antioxidants than thioctic acid. Those characteristic properties thus render the compounds of the invention of potential use in the treatment and prevention of pathologies that on the one hand are associated with ageing, especially cerebral ageing, and on the other hand result from oxidation stress.

The compounds of the invention accordingly constitute therapeutic agents that are capable of combating cognitive disorders associated with cerebral ageing or neurodegenerative disorders, and also combating neurone death associated not only with acute neurodegenerative disorders such as, for example, ischaemia and epilepsy, but also with progressive neurodegenerative disorders, such as, for example, Alzheimer's disease, Pick's disease or neurodegeneracies of the basal ganglia.

In addition to the fact that the compounds of the present invention are new, they have proved to be more powerful antioxidants than thioctic acid.

DETAILED DESCRIPTION OF THE INVENTION

More specifically, the compounds of the present invention are compounds of formula (I):

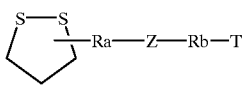

wherein:
Ra represents a linear or branched $(C_1-C_8)$alkylene group,
Rb represents a single bond or a linear or branched $(C_1-C_6)$alkylene group,
Z represents
a thiocarbamate group

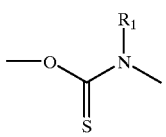

wherein the oxygen atom is bonded to the Ra group,
and $R_1$ represents a hydrogen atom, a linear or branched $(C_1-C_6)$alkyl group, an aryl group or an aryl-$(C_1-C_6)$alkyl group in which the alkyl moiety is linear or branched, or
a thioamide group

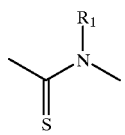

wherein the thiocarbonyl group is bonded to the Ra group, and $R_1$ is as defined hereinbefore,
T represents a group

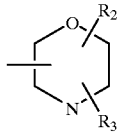

wherein $R_2$ and $R_3$, which may be identical or different, each independently of the other represents a group selected from:
a hydrogen atom, a linear or branched $(C_1-C_6)$alkyl group, a cycloalkyl group, a cycloalkyl-$(C_1-C_6)$alkyl group in which the alkyl moiety is linear or branched, a heterocycloalkyl group, a heterocycloalkyl-$(C_1-C_6)$alkyl group in which the alkyl moiety is linear or branched, an aryl group, an aryl-$(C_1-C_6)$alkyl group in which the alkyl moiety is linear or branched, a heteroaryl group, a heteroaryl-$(C_1-C_6)$-alkyl group in which the alkyl moiety is linear or branched, and an amino-$(C_1-C_6)$-alkyl group in which the alkyl moiety is linear or branched (the amino moiety being optionally substituted by one or two identical or different groups selected from linear or branched $(C_1-C_6)$alkyl, aryl and aryl-$(C_1-C_6)$alkyl in which the alkyl moiety is linear or branched),
their isomers, and addition salts thereof with a pharmaceutically acceptable acid or base.

"Cycloalkyl" is understood to mean a mono- or bi-cyclic, saturated or unsaturated group having from 3 to 8 carbon atoms, each of those groups being optionally substituted by one or more identical or different groups selected from halogen atoms, hydroxy groups, linear or branched ($C_1$–$C_6$) alkyl groups, linear or branched ($C_1$–$C_6$)alkoxy groups, and amino groups (amino itself optionally substituted by one or two identical or different linear or branched ($C_1$–$C_6$)alkyl groups).

"Heterocycloalkyl" is understood to mean a cycloalkyl group in which one or two carbon atoms have been replaced by a hetero atom selected, identically or differently, from nitrogen, oxygen and sulphur.

"Aryl" is understood to mean a phenyl, naphthyl, indenyl, tetrahydronaphthyl, dihydronaphthyl or indanyl group, each of those groups being optionally substituted by one or more identical or different groups selected from halogen atoms, linear or branched ($C_1$–$C_6$)alkyl groups, hydroxy groups, linear or branched ($C_1$–$C_6$)alkoxy groups, amino groups, mono- or di-($C_1$–$C_6$)alkyl-amino groups in which the (each) alkyl moiety is linear or branched, carboxy groups, and linear or branched ($C_1$–$C_6$)alkoxycarbonyl groups.

"Heteroaryl" is understood to mean an aryl group in which one or two carbon atoms have been replaced by a hetero atom selected, identically or differently, from oxygen, nitrogen and sulphur.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The preferred compounds of the invention are compounds of formula (I) wherein the 1,2-dithiolane ring is substituted in the 3-position.

The preferred group Z of the compounds of the invention is the thiocarbamate group

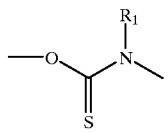

wherein $R_1$ is as defined for formula (I).

According to an advantageous embodiment, the preferred compounds of the invention are compounds of formula (I) wherein Z represents a thiocarbamate group

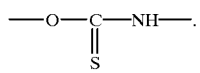

The preferred group T of the compounds of the invention is the group

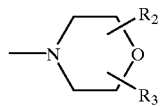

wherein $R_2$ and $R_3$ are as defined for formula (I) and advantageously $R_2$ and $R_3$ each represents a hydrogen atom.

The preferred compounds of the invention are the compounds of formula (I) corresponding to 5-(1,2-dithiolan-3-yl)pentyl N-(2-morpholinoethyl) thiocarbamate hydrochloride, 5-[(3S)-1,2-dithiolan-3-yl]pentyl N-(2-morpholinoethyl) thiocarbamate hydrochloride, 5-[(3R)-1,2-dithiolan-3-yl]pentyl N-(2-morpholinoethyl) thiocarbamate hydrochloride, 5-(1,2-dithiolan-3-yl)pentyl N-(3-morpholinopropyl) thiocarbamate hydrochloride, and 5-(1,2-dithiolan-4-yl)pentyl N-(2-morpholinoethyl) thiocarbamate hydrochloride.

The isomers and the addition salts with a pharmaceutically acceptable acid or base of the preferred compounds form an integral part of the invention.

The invention relates also to a process for the preparation of compounds of formula (I) characterised in that there is used as starting material:

a compound of formula (II):

wherein Ra is as defined for formula (I), which compound of formula (II) is treated in a basic medium with a compound of formula (III):

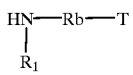

wherein $R_1$, Rb and T are as defined for formula (I), to yield compounds of formula (IV):

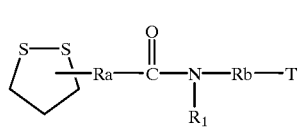

wherein Ra, Rb, $R_1$ and T are as defined hereinbefore, which is subjected to the action of Lawesson's reagent, to yield compounds of formula (I/a), a particular case of the compounds of formula (I):

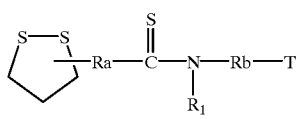

wherein Ra, Rb, R₁ and T are as defined hereinbefore, or a compound of formula (V)

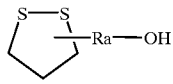

wherein Ra is as defined for formula (1),
which is reacted, in the presence of bis(tributyltin) oxide, with a thioisocyanate of formula (VI):

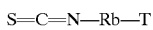

wherein Rb and T are as defined for formula (I),
to yield compounds of formula (I/b), a particular case of the compounds of formula (I):

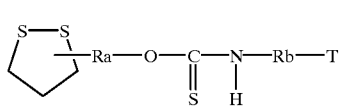

wherein Ra, Rb and T are as defined hereinbefore,
which compounds of formula (I/b) are treated, if desired, with a compound of formula (VII):

wherein R₁ is as defined for formula (I) and X represents a halogen atom,
to yield compounds of formula (I/c), a particular case of the compounds of formula (I):

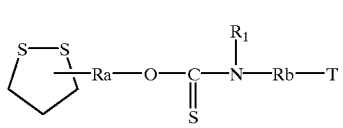

wherein Ra, Rb, R₁ and T are as defined hereinbefore, which compounds (I/a) to (I/c) constitute the totality of the compounds of the invention, are purified, if necessary, according to a conventional purification technique, may be separated, if desired, into their different isomers according to a conventional separation technique, and are converted, where appropriate, into addition salts thereof with a pharmaceutically acceptable acid or base.

The compounds of formulae (II), (III), (V), (VI) and (VII) are either commercial compounds or are obtained according to known conventional methods of organic synthesis.

The present invention relates also to pharmaceutical compositions comprising as active ingredient at least one compound of formula (1), an optical isomer thereof or an addition salt thereof with a pharmaceutically acceptable acid or base, on its own or in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragees, sublingual tablets, sachets, gelatin capsules, lozenges, suppositories, creams, ointments, dermal gels, injectable or drinkable preparations, aerosols, eye or nose drops, etc.

The useful dosage varies according to the age and weight of the patient, the route of administration, the nature and severity of the disorder, and whether any other treatments are being taken, and ranges from 10 mg to 500 mg in one or more administrations daily.

The following Examples illustrate the invention but do not limit it in any way.

The starting materials used are known products or are prepared according to known procedures.

EXAMPLE 1

5-(1,2-Dithiolan-3-yl) N-[2-(4-morpholinyl)ethyl] pentane Thioamide Hydrochloride Step A: 5-(1,2-Dithiolan-3-yl) N-[2-(4-morpholinyl)ethyl] pentanamide 4.5 g of hydroxybenzotriazole, 10.5 g of 2-(1H-benzotriazol-1-yl)-1,1,3,3-tetramethyluronium tetrafluoroborate, 7.8 g of diisopropylethylamine and 3.9 g of 2-morpholino-1-ethylamine are added at room temperature to a solution of 6.2 g of thioctic acid in 180 ml of tetrahydrofuran. After 20 hours, the reaction mixture is concentrated under reduced pressure. The residue is taken up in ethyl acetate, washed and then dried over Na₂SO₄. Concentration under reduced pressure yields 8.4 g of the expected product.

Step B: 5-(1,2-Dithiolan-3-yl) N-[2-(4-morpholinyl)ethyl] pentane thioamide hydrochloride A solution of 8.3 g of the compound obtained in Step A and 5.3 g of Lawesson's reagent in 250 ml of toluene is maintained at 80° C. for 4 hours. The reaction mixture is then cooled and extracted with a 1N hydrochloric acid solution The aqueous phase is then rendered alkaline by the addition of Na₂CO₃ and then extracted with ethyl acetate. The combined organic phases are dried and then concentrated under reduced pressure. The residue is then taken up in ethanol, rendered acidic and concentrated again. After the addition of ether, trituration and filtering off the final residue, the expected product is isolated.

Elemental microanalysis:

|  | C | H | N | S | Cl |
|---|---|---|---|---|---|
| % calculated | 45.32 | 7.33 | 7.55 | 25.93 | 9.56 |
| % found | 45.24 | 7.23 | 7.61 | 25.75 | 9.48 |

Melting point: 98–100° C.

EXAMPLE 2

5-(1,2-Dithiolan-3-yl)pentyl N-(2-morpholinoethyl) Thiocarbamate Hydrochloride

A solution of 9.6 g of 5-(1,2-dithiolan-3-yl)-1-pentanol and 30 g of bis(tributyltin) oxide in 400 ml of toluene is refluxed for 20 hours and then cooled to 60° C. 1.2 equivalents of 2-(morpholin-4-yl)-1-ethyl isocyanate are then added and the reaction mixture is maintained at 60° C. for 22 hours. After cooling, extraction is carried out with a 1N hydrochloric acid solution. The aqueous phase is then neutralised and subsequently extracted with ethyl acetate, and the combined organic phases are dried and then concentrated under reduced pressure. Chromatography over silica gel (dichloromethane/tetrahydrofuran/95/5) enables the expected product to be isolated.

Elemental microanalysis:

|  | C | H | N | S | Cl |
|---|---|---|---|---|---|
| % calculated | 43.94 | 7.37 | 6.83 | 23.46 | 8.65 |
| % found | 43.70 | 7.55 | 7.05 | 21.31 | 9.34 |

Melting point: 105–110° C.

EXAMPLE 3

(R)-5-(1,2-Dithiolan-3-yl)pentyl N-(2-morpholinoethyl) Thiocarbamate Hydrochloride The procedure is as for Example 2 using (R)-5-(1,2-dithiolan-3-yl)-1-pentanol as substrate.

Elemental microanalysis:

|  | C | H | N | S | Cl |
|---|---|---|---|---|---|
| % calculated | 44.92 | 7.29 | 6.98 | 23.98 | 8.84 |
| % found | 44.72 | 7.27 | 6.90 | 24.19 | 8.79 |

Melting point: 108–110° C.

EXAMPLE 4

(S)-5-(1,2-Dithiolan-3-yl)pentyl N-(2-morpholinoethyl) Thiocarbamate Hydrochloride The procedure is as for Example 2 using (S)-5-(1,2-dithiolan-3-yl)-1-pentanol as substrate.

Elemental microanalysis:

|  | C | H | N | S | Cl |
|---|---|---|---|---|---|
| % calculated | 44.92 | 7.29 | 6.99 | 8.84 | 23.98 |
| % found | 44.08 | 7.49 | 6.88 | 8.84 | 24.00 |

Melting point: 112–116° C.

EXAMPLE 5

5-(1,2-Dithiolan-3-yl)pentyl N-(2-morpholinopropyl) Thiocarbamate Hydrochloride

The procedure is as for Example 2 using 3-(morpholin-4-yl)-1-propyl thioisocyanate as reagent.

Elemental microanalysis:

|  | C | H | N | S | Cl |
|---|---|---|---|---|---|
| % calculated | 46.30 | 7.53 | 6.75 | 23.17 | 8.54 |
| % found | 46.24 | 7.41 | 6.65 | 22.76 | 8.47 |

Melting point: 86–88° C.

EXAMPLE 6

5-(1,2-Dithiolan-4-yl)pentyl N-(2-morpholinoethyl) Thiocarbamate Hydrochloride

The procedure is as for Example 2 using 5-(1,2-dithiolan-4-yl)-1-pentanol as substrate.

Elemental microanalysis:

|  | C | H | N | S | Cl |
|---|---|---|---|---|---|
| % calculated | 44.92 | 7.29 | 6.98 | 23.98 | 8.81 |
| % found | 44.50 | 7.56 | 7.27 | 24.17 | 8.84 |

Meltingpoint: 80–85° C.

EXAMPLE 7

5-(1,2-Dithiolan-3-yl)pentyl N-[2-(3,5-dimethyl)morpholinoethyl] Thiocarbamate

The procedure is as for Example 2 using 4-(2-isothiocyanatoethyl)-3,5-dimethylmorpholine as reagent.

EXAMPLE 8

N-[2-(4-Benzyl-2-morpholinyl)ethyl]-5-(1,2-dithiolan-3-yl)pentane Thioamide

The procedure is as for Example 1, Steps A and B, using 2-(4-benzyl-2-morpholinyl)ethylamine as reagent in Step A.

PHARMACOLOGICAL STUDY OF THE COMPOUNDS OF THE INVENTION

EXAMPLE 9

Cytotoxicity test using L-homocysteine

This test allows the in vitro evaluation of the neuroprotective properties of the test compounds by determining their capacity to combat the cytotoxicity caused by the exposure of murine HT 22 hippocampal cells to L-homocysteine (*Neuron;* 2, 1989, 1547–1885).

Murine HT 22 hippocampal cells in culture are preincubated for 1 hour in the presence of seven concentrations (5, 10, 25, 50, 75, 100 and 200 $\mu$M) of the "anti-oxidation" agent studied. The cell cultures are then exposed for 48 hours to 2 mM L-homocysteine in the presence or absence of anti-oxidation agents. The cytotoxicity is evaluated by the 3-(4,5-dimethylthiazol-2-yl)-2,5-diphenyl-tetrazolium bromide reduction method (*Immunol. Methods.,* 1983, 65, 55–63). The results are expressed as $PC_{50}$, the concentration that represents 50% protection compared with the cytotoxicity measured in the cell cultures in the absence of anti-oxidation agents. In this test, the compound of Example 2 has a $PC_{50}$ of 15.5 $\mu$M.

EXAMPLE 10

Measurement of Lipid Peroxidation

The cortex membranes of the male NMRI mouse (1 g/20 ml in Tris HCl 20 mM pH 7.4) are preincubated for 15 minutes at 37° C. with the anti-oxidation agent being studied at a concentration of 5 mM. The membranes are then exposed for 15 minutes to $FeSO_4$ (100 μM)/ascorbic acid (1000 μM)/$H_2O_2$ (1000 μM). The reaction is stopped with trichloroacetic acid (20% v/v) at +4° C., and then the sample is centrifuged at 1500 g for 5 min at +4° C. An equivalent volume (1 ml) of thiobarbituric acid (0.67%) is then added to the supernatant and incubated at +100° C. for 20 minutes. The reaction is stopped over ice. The solution is read at 532 nm using a spectrophotometer (determination of the concentrations of malondialdehyde, expressed as TBARS). A standard range of malondialdehyde (0–40 μM) is established for each experiment. For each anti-oxidation agent tested, the results are expressed as a percentage of inhibition compared with the control ($FeSO_4$/ascorbic acid/$H_2O_2$) on its own. In this test, the compound of Example 2 exhibits an inhibition of 90%.

EXAMPLE 11

Lethality Test

This test allows the in vivo determination of the neuroprotective properties of the test compounds by measuring their capacity to combat the lethality induced in the mouse by the intracerebroventricular administration of tert-butyl hydroperoxide, an oxidizing agent capable of causing neurodegeneracies of the apoptotic type (*Free radical Biol. Med.*, 1993, 15, 195–202 and *Mol. Chem. Neuropathol.*, 1991, 26, 95–106).

Intracerebroventricular administration of tert-butyl hydroperoxide (1 μl of a 70% solution) causes lethality in the male NMRI mouse (30–35 g). The lethality is measured two hours after the administration of tert-butyl hydroperoxide and is expressed as a percentage of protection compared with the lethality in the animals that have been given the carrier of the "anti-oxidation" agents studied. The latter are administered by the intraperitoneal route in a dose of 150 mg/kg 30 minutes before the administration of tert-butyl hydroperoxide. In this test, the compound of Example 2 provides 100% protection.

EXAMPLE 12

Hyperglycaemia Induced by Alloxane in the NMRI Mouse

In the male NMRI mouse (30–35 g; fasted for 18–24 hours) the intravenous administration of alloxane (40 mg/kg) causes hyperglycaemia measured 24 hours after the administration of alloxane. The hyperglycaemia is determined by measuring the D-glucose in the plasma as a percentage of inhibition of the hyperglycaemia in the animals that were given the "anti-oxidation" agent (administered per os at 400 mg/kg 1 or 3 hours before the alloxane) compared with the animals treated with alloxane on its own. The compound of Example 2 also inhibits hyperglycaemia by 100% (administration at 1 hour before) and by 92% (administration at 3 hours before).

What is claimed is:
1. A compound selected from those of the formula (I):

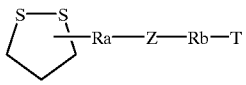

(I)

wherein:
Ra represents linear or branched ($C_1$–$C_8$)alkylene,
Rb represents a single bond, or linear or branched ($C_1$–$C_6$) alkylene,
Z represents:
thiocarbamate

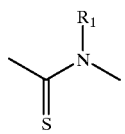

wherein the oxygen is bonded to Ra, and $R_1$ represents a group selected from hydrogen, linear or branched ($C_1$–$C_6$) alkyl, aryl, and aryl-($C_1$–$C_6$)alkyl in which alkyl is linear or branched, or
the thioamide

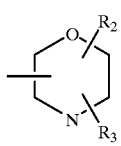

wherein thiocarbonyl is bonded to Ra, and $R_1$ is as defined hereinbefore,

T represents a group

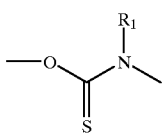

wherein $R_2$ and $R_3$, which may be identical or different, each independently of the other represents a group selected from hydrogen, linear or branched ($C_1$–$C_6$) alkyl, cycloalkyl, cycloalkyl-($C_1$–$C_6$) alkyl in which alkyl is linear or branched, heterocycloalkyl, heterocycloalkyl-($C_1$–$C_6$)alkyl in which alkyl is linear or branched, aryl, aryl-($C_1$–$C_6$)alkyl in which alkyl is linear or branched, heteroaryl, heteroaryl-($C_1$$C_6$)alkyl in which alkyl is linear or branched, and amino-($C_1$–$C_6$)alkyl in which alkyl is linear or branched (amino being optionally substituted by one or two identical or different groups selected from linear or branched ($C_1$–$C_6$)alkyl, aryl, and aryl-($C_1$–$C_6$)alkyl in which alkyl is linear or branched),
its isomers, and pharmaceutically-acceptable acid or base addition salts thereof, it being understood that:
"cycloalkyl" means a mono- or bi-cyclic, saturated or unsaturated group having 3 to 8 carbon atoms, each of those groups being optionally substituted by one or more identical or different groups selected from halogen, hydroxy, linear or branched ($C_1$–$C_6$)alkyl, linear or branched ($C_1$–$C_6$)alkoxy, and amino (amino itself optionally substituted by one or two, identical or different linear or branched ($C_1$–$C_6$)alkyl), "heterocycloalkyl" means cycloalkyl in which one or two carbon atoms have been replaced by a heteroatom selected, identically or differently, from nitrogen, oxygen, and sulphur, "aryl" means phenyl, naphthyl, indenyl, tetrahydronaphthyl, dihydronaphthyl, or indanyl, each of those groups being optionally substituted by one or more, identical or different, groups selected from halogen, linear or branched ($C_1$–$C_6$)alkyl, hydroxy, linear or branched ($C_1$–$C_6$)alkoxy, amino, mono- or di-($C_1$–$C_6$)alkyl-amino in which alkyl moiety is linear or branched, carboxy, and linear or branched ($C_1$–$C_6$) alkoxycarbonyl, "heteroaryl" means aryl in which one or two carbon atoms have been replaced by a heteroatom selected, identically or differently, from oxygen, nitrogen, and sulphur.

2. A compound of claim 1, selected from those of formula (IA):

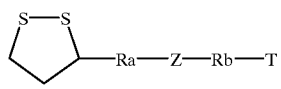

(IA)

wherein

Ra represents linear or branched ($C_1$–$C_8$)alkylene,

Rb represents a single bond, or linear or branched ($C_1$–$C_6$) alkylene,

Z represents:
thiocarbamate

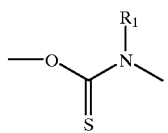

wherein the oxygen is bonded to Ra, and $R_1$ represents a group selected from hydrogen, linear or branched ($C_1$–$C_6$) alkyl, aryl, and aryl-($C_1$–$C_6$)alkyl in which alkyl is linear or branched, or thioamide

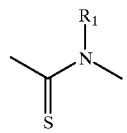

wherein the thiocarbonyl is bonded to Ra, and $R_1$ is as defined hereinbefore,

T represents a group

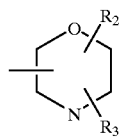

wherein $R_2$ and $R_3$, which may be identical or different, each independently of the other represents a group selected from hydrogen, linear or branched ($C_1$–$C_6$) alkyl, cycloalkyl, cycloalkyl-($C_1$–$C_6$)alkyl in which alkyl is linear or branched, heterocycloalkyl, heterocycloalkyl-($C_1$–$C_6$)alkyl in which alkyl is linear or branched, aryl, aryl-($C_1$–$C_6$)alkyl in which alkyl is linear or branched, heteroaryl, heteroaryl-($C_1$–$C_6$)alkyl in which alkyl is linear or branched, and amino-($C_1$–$C_6$)alkyl in which alkyl is linear or branched (amino being optionally substituted by one or two, identical or different, groups selected from linear or branched ($C_1$–$C_6$)alkyl, aryl, and aryl-($C_1$–$C_6$)alkyl in which alkyl is linear or branched), its isomers, and pharmaceutically-acceptable acid or base addition salts thereof.

3. A compound of claim 1, selected from those of formula (IB):

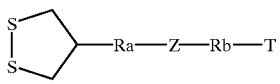

(IB)

wherein:

Ra represents linear or branched ($C_1$–$C_8$)alkylene,

Rb represents a single bond, or linear or branched ($C_1$–$C_6$) alkylene,

Z represents:
thiocarbamate

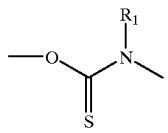

wherein the oxygen is bonded to Ra, and $R_1$ represents a group selected from hydrogen, linear or branched ($C_1$–$C_6$) alkyl, aryl, and aryl-($C_1$–$C_6$)alkyl in which alkyl is linear or branched, or thioamide

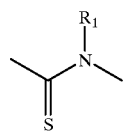

wherein the thiocarbonyl is bonded to Ra, and $R_1$ is as defined hereinbefore,

T represents a group:

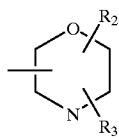

wherein $R_2$ and $R_3$, which may be identical or different, each independently of the other represents a group selected from hydrogen, linear or branched ($C_1$–$C_6$) alkyl, cycloalkyl, cycloalkyl-($C_1$–$C_6$)alkyl in which alkyl is linear or branched, heterocycloalkyl, heterocycloalkyl-($C_1$–$C_6$)alkyl in which alkyl is linear or branched, aryl, aryl-($C_1$–$C_6$)alkyl in which alkyl is linear or branched, heteroaryl, heteroaryl-($C_1$–$C_6$)alkyl in which alkyl is linear or branched, and amino-($C_1$–$C_6$)alkyl in which alkyl is linear or branched (amino being optionally substituted by one or two, identical or different, groups selected from linear or branched ($C_1$–$C_6$)alkyl, aryl, and aryl-($C_1$–$C_6$)alkyl in which alkyl is linear or branched), its isomers, and pharmaceutically-acceptable acid or base addition salts thereof.

4. A compound of claim 1, wherein Z represents thiocarbamate

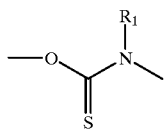

wherein $R_1$ is as defined for formula (I), its isomers, and pharmaceutically-acceptable acid or base addition salts thereof.

5. A compound of claim 1, wherein Z represents thiocarbamate

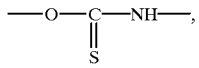

its isomers, and pharmaceutically-acceptable acid or base addition salts thereof.

6. A compound of claim 1, wherein T represents

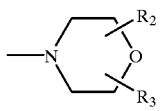

wherein $R_2$ and $R_3$ are as defined for formula (I), its isomers, and pharmaceutically-acceptable acid or base addition salts thereof.

7. A compound of claim 6, wherein $R_2$ and $R_3$, which are identical, represent hydrogen, its isomers, and pharmaceutically-acceptable acid or base addition salts thereof.

8. A compound of claim 1, which is 5-(1,2-dithiolan-3-yl)pentyl N-(2-morpholinoethyl) thiocarbamate hydrochloride.

9. A compound of claim 1, which is 5-[(3S)-1,2-dithiolan-3-yl]pentyl N-(2 -morpholinoethyl) thiocarbamate hydrochloride.

10. A compound of claim 1, which is 5-[(3R)-1,2-dithiolan-3-yl]pentyl N-(2-morpholinoethyl) thiocarbamate hydrochloride.

11. A compound of claim 1, which is 5-(1,2-dithiolan-3-yl)pentyl N-(3-morpholinopropyl) thiocarbamate hydrochloride.

12. A compound of claim 1, which is 5-(1,2-dithiolan-4-yl)pentyl N-(2-morpholinoethyl) thiocarbamate hydrochloride.

13. A method for treating a living body afflicted with a condition which requires the use of anti-oxidation agent, comprising the step of administering to the living body an amount of a compound of claim 1, which is effective for alleviation of said condition.

14. A pharmaceutical composition comprising as active principle an effective anti-oxidation amount of a compound as claimed in claim 1, in combination with one or more pharmaceutically-acceptable excipients or carriers.

* * * * *

UNITED STATES PATENT AND TRADEMARK OFFICE
CERTIFICATE OF CORRECTION

PATENT NO. : 6,150,358
DATED : Nov. 21, 2000
INVENTOR(S) : S. Goldstein, C. Guillonneau, Y. Charton, P. Lestage, B. Lockhart It is certified that error appears in the above-identified patent and that said Letters Patent is hereby corrected as shown below:

Front Page, [56] References Cited, U.S. PATENT
    DOCUMENTS: "514/445" should read:
    -- 514/440 --. Form PTO 892, U.S. Patent
    Documents, Item A.

Column 7, line 7: "/tetrahydrofiran" should read:
    -- /tetrahydrofuran --. Page 9, line 14

Column 10, line 37(approx): Insert -- the --
    between "wherein" and "thiocarbonyl".
    Preliminary Amendment dtd 12/14/99, Claim 1,
    line 11 on page 15.

Column 11, line 16: Delete the word "moiety".
    Preliminary Amendend dtd 12/14/99, Claim 1,
    line 21 on page 15.

Column 13, line 21: "$(C_{1-6})$alkyl" should read:
    -- $(C_1-C_6)$alkyl --. Page 18, line 3

Signed and Sealed this

Eighth Day of May, 2001

Attest:

NICHOLAS P. GODICI

Attesting Officer    Acting Director of the United States Patent and Trademark Office